United States Patent
Verma et al.

(10) Patent No.: US 12,186,139 B2
(45) Date of Patent: Jan. 7, 2025

(54) SYSTEMS AND METHODS FOR SCENE-ADAPTIVE IMAGE QUALITY IN SURGICAL VIDEO

(71) Applicant: Verily Life Sciences LLC, South San Francisco, CA (US)

(72) Inventors: Nishant Verma, Burlingame, CA (US); Ryan Robertson, Sunnyvale, CA (US); Thomas Teisseyre, Montara, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 327 days.

(21) Appl. No.: 17/663,034

(22) Filed: May 12, 2022

(65) Prior Publication Data

US 2022/0370167 A1   Nov. 24, 2022

Related U.S. Application Data

(60) Provisional application No. 63/191,481, filed on May 21, 2021.

(51) Int. Cl.
*A61B 90/00* (2016.01)
*A61B 1/00* (2006.01)
(Continued)

(52) U.S. Cl.
CPC ...... *A61B 90/361* (2016.02); *A61B 1/000096* (2022.02); *A61B 1/0661* (2013.01);
(Continued)

(58) Field of Classification Search
CPC ............ A61B 90/361; A61B 1/000096; A61B 1/0661; A61B 90/37; A61B 34/37;
(Continued)

(56) References Cited

U.S. PATENT DOCUMENTS

| 8,428,308 B2 | 4/2013 | Jasinski et al. |
| 2003/0159141 A1 | 8/2003 | Zacharias |

(Continued)

FOREIGN PATENT DOCUMENTS

| EP | 3135028 | 1/2019 |
| JP | 5981053 | 8/2016 |

OTHER PUBLICATIONS

Huang et al., "Feature Extraction of Video Data for Automatic Visual Tool Tracking in Robot Assisted Surgery", Proceedings of the 2019 4th International Conference on Robotics, Control and Automation, Available Online at URL: https://dl.acm.org/doi/abs/10.1145/3351180.3351185, Jul. 2019, pp. 121-127.

(Continued)

*Primary Examiner* — Juan A Torres
(74) *Attorney, Agent, or Firm* — Kilpatrick Townsend & Stockton LLP

(57) ABSTRACT

One example method for scene-adaptive image quality in surgical video includes receiving a first video frame from an endoscope, the first video frame generated from a first raw image captured by an image sensor of the endoscope and processed by an image signal processing ("ISP") pipeline having a plurality of ISP parameters; recognizing, using a trained machine learning ("ML") model, a first scene type or a first scene feature type based on the first video frame; determining a first set of ISP parameters based on the first scene type or the first scene feature type; applying the first set of ISP parameters to the ISP pipeline; and receiving a second video frame from the endoscope, the second video frame generated from a second raw image captured by the image sensor and processed by the ISP pipeline using the first set of ISP parameters.

24 Claims, 8 Drawing Sheets

(51) Int. Cl.
*A61B 1/06* (2006.01)
*G06T 7/00* (2017.01)

(52) U.S. Cl.
CPC ............ *A61B 90/37* (2016.02); *G06T 7/0012* (2013.01); *G06T 2207/10068* (2013.01)

(58) Field of Classification Search
CPC ............ A61B 1/000094; A61B 1/0005; A61B 1/000095; G06T 7/0012; G06T 2207/10068; G06T 2207/20081; G06T 2207/30168; G06T 7/0002
USPC ......................................................... 382/128
See application file for complete search history.

(56) References Cited

U.S. PATENT DOCUMENTS

| | | |
|---|---|---|
| 2007/0273759 A1 | 11/2007 | Krupnick et al. |
| 2013/0142418 A1 | 6/2013 | Van Zwol et al. |
| 2016/0344996 A1 | 11/2016 | Olilla |
| 2017/0270508 A1 | 9/2017 | Roach et al. |
| 2019/0110856 A1* | 4/2019 | Barral ..................... A61B 90/37 |
| 2019/0182421 A1* | 6/2019 | Piponi ..................... H04N 1/62 |
| 2020/0304650 A1 | 9/2020 | Roach et al. |
| 2022/0301123 A1* | 9/2022 | Mosleh .................. G06F 18/214 |
| 2023/0255443 A1* | 8/2023 | He ......................... H04N 23/74 |
| | | 600/102 |

OTHER PUBLICATIONS

Kim et al., "Designing a New Endoscope for Panoramic-View with Focus-Area 3D-Vision in Minimally Invasive Surgery", Journal of Medical and Biological Engineering, vol. 40, Available Online at URL: https://link.springer.com/article/10.1007/s40846-019-00503-9, Dec. 3, 2019, pp. 204-219.

International Application No. PCT/US2022/072322 , "International Search Report and Written Opinion", Jul. 29, 2022, 11 pages.

* cited by examiner

SYSTEMS AND METHODS FOR SCENE-ADAPTIVE IMAGE QUALITY IN SURGICAL VIDEO

CROSS-REFERENCE TO RELATED APPLICATIONS

This application claims priority to U.S. Provisional Patent Application No. 63/191,481, filed May 21, 2022, titled "Systems And Methods For Scene-Adaptive Image Quality In Surgical Video," the entirety of which is hereby incorporated by reference" is changed to "This application claims priority to U.S. Provisional Patent Application No. 63/191,481, filed May 21, 2021, titled "Systems And Methods For Scene-Adaptive Image Quality In Surgical Video," the entirety of which is hereby incorporated by reference

FIELD

The present application generally relates to image processing and more particularly relates to systems and methods for scene-adaptive image quality in surgical video.

BACKGROUND

Endoscopes are routinely used in surgical procedures to illuminate anatomy and to capture video during the procedure. However, the quality of the video can vary significantly due to illumination in the scene, which can be affected by anatomical features or instruments in the scene. In addition, depending on the anatomical features in the scene, different image settings, e.g., brightness, contrast, etc., may be desirable to provide a better view to the surgeon. To enable the surgeon to adjust these settings, the system may provide controls to make such adjustments, e.g., on-screen controls or physical dials or knobs.

SUMMARY

Various examples are described for systems and methods for scene-adaptive image quality in surgical video. One example method for scene-adaptive image quality in surgical video includes receiving a first video frame from an endoscope, the first video frame generated from a first raw image captured by an image sensor of the endoscope and processed by an image signal processing ("ISP") pipeline having a plurality of ISP parameters; recognizing, using a trained machine learning ("ML") model, a first scene type or a first scene feature type based on the first video frame; determining a first set of ISP parameters based on the first scene type or the first scene feature type; applying the first set of ISP parameters to the ISP pipeline; and receiving a second video frame from the endoscope, the second video frame generated from a second raw image captured by the image sensor and processed by the ISP pipeline using the first set of ISP parameters.

One example system includes a non-transitory computer-readable medium; and one or more processors communicatively coupled to the non-transitory computer-readable medium and configured to execute processor-executable instructions stored in the non-transitory computer-readable medium to receive a first video frame from an endoscope, the first video frame generated from a first raw image captured by an image sensor of the endoscope and processed by an image signal processing ("ISP") pipeline having a plurality of ISP parameters; recognize, using a trained machine learning ("ML") model, a first scene type or a first scene feature type based on the first video frame; determine a first set of ISP parameters based on the first scene type or the first scene feature type; apply the first set of ISP parameters to the ISP pipeline; and receive a second video frame from the endoscope, the second video frame generated from a second raw image captured by the image sensor and processed by the ISP pipeline using the first set of ISP parameters.

One example non-transitory computer-readable medium includes processor-executable instructions configured to cause one or more processors to receive a first video frame from an endoscope, the first video frame generated from a first raw image captured by an image sensor of the endoscope and processed by an image signal processing ("ISP") pipeline having a plurality of ISP parameters; recognize, using a trained machine learning ("ML") model, a first scene type or a first scene feature type based on the first video frame; determine a first set of ISP parameters based on the first scene type or the first scene feature type; apply the first set of ISP parameters to the ISP pipeline; and receive a second video frame from the endoscope, the second video frame generated from a second raw image captured by the image sensor and processed by the ISP pipeline using the first set of ISP parameters.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
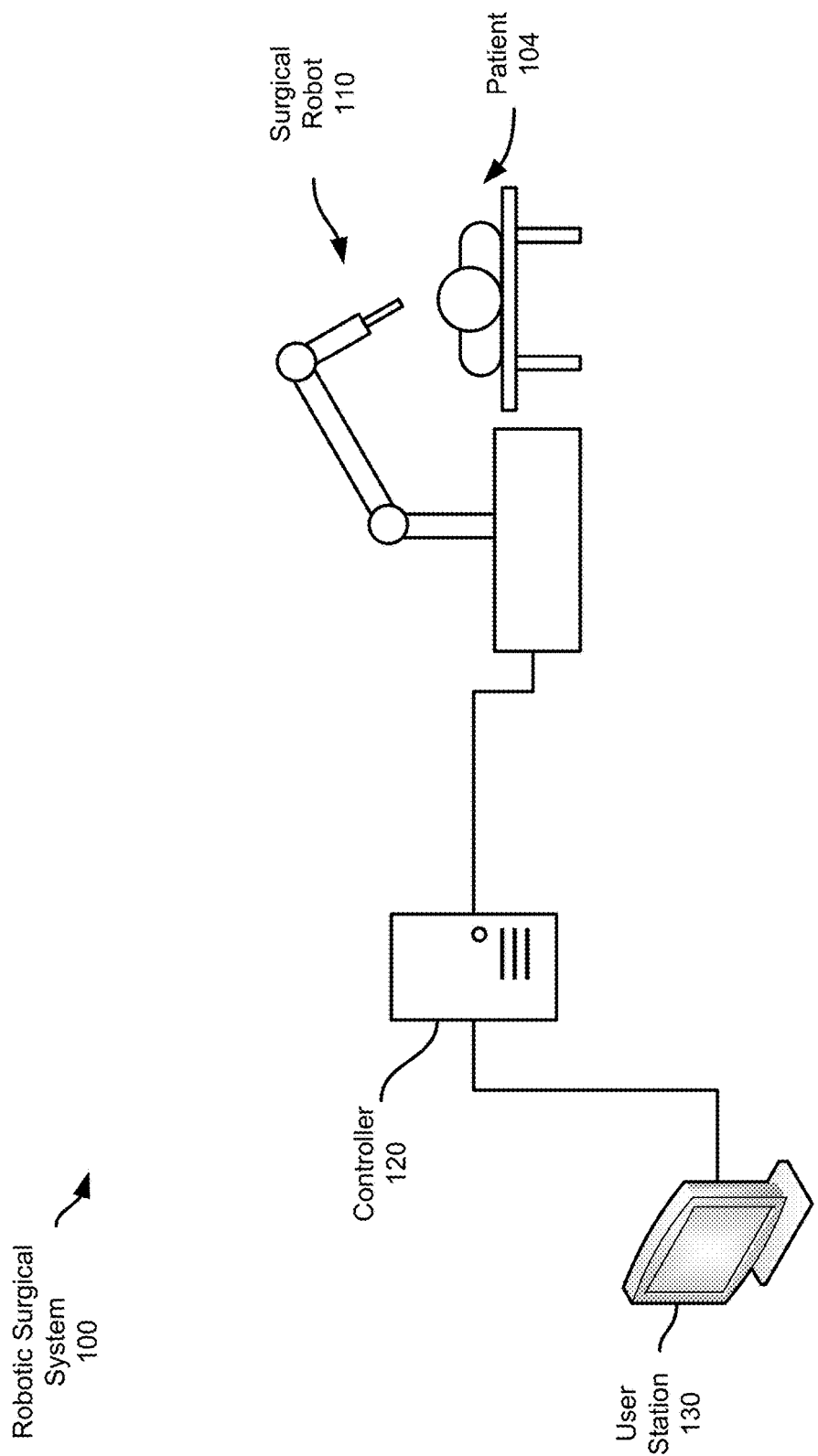
FIG. 1 show example systems for scene-adaptive image quality in surgical video.

Examples are described herein in the context of systems and methods for scene-adaptive image quality in surgical video. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

During a minimally invasive surgery ("MIS"), e.g., one performed using a robotic surgical system, a surgeon may employ an endoscope to capture video within the surgical site to allow them to view the surgical site, to guide tool movement, and to detect potential complications. The surgeon sits at a surgeon console and manipulates hand or foot controls to guide the movement of robotic tools within the surgical site, while watching video captured by the endoscope. However, as the surgeon performs the surgery, lighting within the scene may change, such as due to movement to a new location within the patient's body, introduction of a reflective tool into the scene, darkening due to bleeding, reflection from nearby tissue, etc.

To adjust to these changes, robotic surgical system employs functionality to dynamically adjust image settings in the endoscope to improve or maintain image quality despite changing conditions. As the surgical procedure proceeds and the endoscope captures video, the video is provided to one or more trained machine learning ("ML") models that recognize the current scene type or features in the scene. For example the ML model has been trained to recognize common surgical scenes, such as scenes corresponding to commonly performed surgical procedures (e.g., gastrojejunostomy, appendectomy, cholecystectomy, etc.), commonly occurring anatomy (e.g., liver, gall bladder, abdominal wall, small or large intestine, etc.), surgical tools, events (e.g., bleeding, smoke, etc.), or other features. As the ML model(s) receive frames of video, they analyze some of the frames and output the identified scene types or features, which are used to adjust image signal processing ("ISP") settings in the camera.

To make these adjustments, the system adjusts parameters used by an image sensor processing ("ISP") pipeline employed by the endoscope to convert raw pixel data output by an image sensor into a color image. This example system has access to sets of ISP parameters corresponding to each type of scene or scene feature that the ML model(s) have been trained to recognize. When a particular type of scene is recognized, the corresponding set of ISP parameters may be obtained and provided to the camera to overwrite previous ISP parameters, thereby processing incoming raw image sensor data to provide a higher quality image of the scene. Further, if both a scene type and a scene feature (or multiple scene features) are recognized, the robotic surgical system may combine ISP parameters from multiple different sets to generate a single set of hybrid ISP parameters, which are then applied to the endoscope's camera. As the surgical procedure continues, these ISP parameters may change as the scene changes, e.g., as the endoscope moves through the patient's body, and surgical tools enter and exit the frame, etc.

Thus, the system is able to dynamically adjust the image quality provided to the surgeon in real-time to maintain high video quality throughout the procedure, despite changing conditions. This can provide significantly improved performance over existing endoscopes which instead employ a static set of ISP parameters that are applied to raw image sensor data, irrespective of the scene. Further, by employing ML models to enable scene or scene feature recognition, ISP parameters may be specially tailored for specific scenarios and applied as needed when those scenarios are encountered in real-time. Such functionality may enable a surgeon to more effectively and efficiently perform a surgical procedure by presenting a clearer view of the surgical site.

This illustrative example is given to introduce the reader to the general subject matter discussed herein and the disclosure is not limited to this example. The following sections describe various additional non-limiting examples and examples of systems and methods for scene-adaptive image quality in surgical video.

Referring now to FIG. 1, FIG. 1 shows an example system for scene-adaptive image quality in surgical video. The system includes a robotic surgical system 100 that includes a surgical robot 110 and a user station 130, both of which are connected to a controller 120.

The surgical robot 110 is any suitable robotic system that can be used to perform surgical procedures on a patient, e.g., patient 104, to provide simulations of surgical procedures, or to provide training functionality to allow a surgeon to learn how to control a surgical robot 110, e.g., using exercises to train particular movements or general dexterity, precision, etc. It should be appreciated that discussions throughout this detailed description related to surgical procedures are equally applicable to simulated procedures or training exercises using a surgical robot 110.

A surgical robot 110 may have one or more articulating arms connected to a base. The arms may be manipulated by a controller 120 via inputs received from the user station 130, which may include one or more user interface devices, such as joysticks, knobs, handles, or other rotatable or translatable devices to effect movement of one or more of the articulating arms, as well as one or more display devices to display information to the surgeon during surgery, e.g., video from an endoscope, information from patient medical records, previously obtained images (e.g., X-rays, MRI images, etc.). The articulating arms may be equipped with one or more surgical instruments to perform aspects of a surgical procedure. Different surgical robots 110 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without articulating arms, such as for endoscopy procedures, may be employed according to different examples.

The controller in this example includes a computing device in communication with the surgical robot 110 and is able to control access and use of the robot. For example, the controller 120 may require that a user authenticate herself before allowing access to or control of the surgical robot 110. As mentioned above, the controller 120 may include, or have connected to it, e.g., via user station 130, one or more user input devices capable of providing input to the controller, such as a keyboard, mouse, or touchscreen, capable of controlling the surgical robot 110, such as one or more joysticks, knobs, handles, dials, pedals, etc.

During a surgical procedure, one or more tools may be connected to the surgical robot 110 that may then be inserted into the patient's body to perform different aspects of the surgical procedure. To enable the surgeon to perform the surgery, an endoscope may be connected to the surgical robot 110 and inserted in to the patient 104. Video captured by the endoscope may be communicated to the controller, which then presents them to the surgeon at the user station 130. Based on the video, the surgeon can manipulate the surgical robot to cut tissue, ablate, cauterize, etc.

To help ensure the surgeon is provided with a high-quality view of the surgical scene, the controller 120 executes one or more trained ML models to analyze the incoming video from the endoscope, select ISP parameters based on the ML models' output, and updates an "ISP pipeline," described in greater detail below, for the endoscope's camera with the updated ISP parameters. In this example, the ISP pipeline is implemented on the controller 120, such as using software executed by the controller's processor or by using a special-purpose processor, such as a graphics processing unit ("GPU"), field programmable gate array ("FPGA"), etc. In some such examples, raw video frames are received from the endoscope camera and processed by the controller. However, in some examples, the ISP pipeline may be implemented in the endoscope itself. The new ISP parameters are then used on subsequent captured video to process incoming raw image sensor information.

Figure 2:
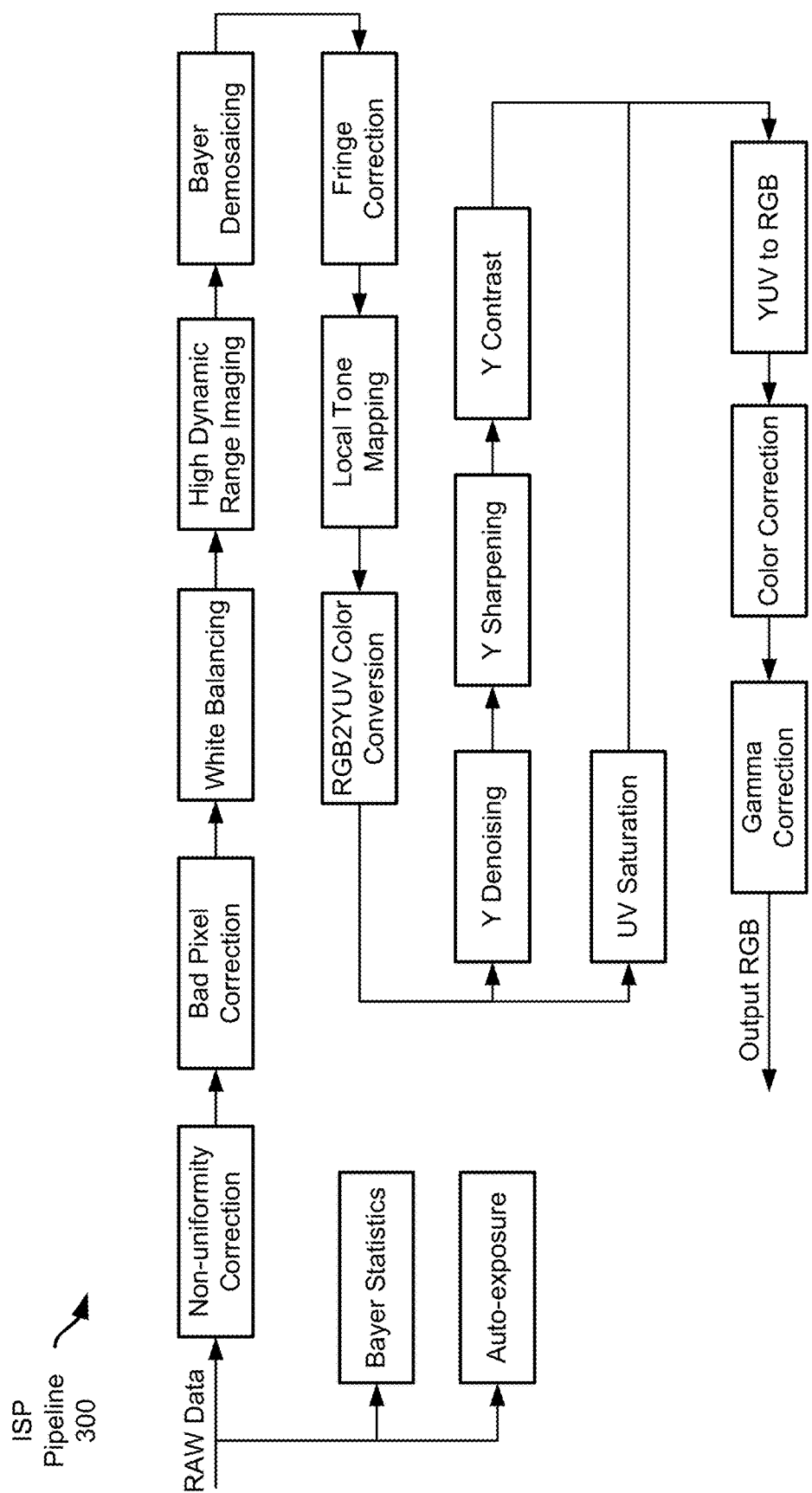
FIG. 2 shows an image signal processing pipeline to convert raw image sensor information to a color image.

To provide video, the endoscope employs an image sensor that includes an array of light-sensitive elements, e.g., photodiodes, that outputs a grayscale RAW-format image, such as in a grid Bayer pattern. This RAW-format image is then passed through a series of image and signal processing steps to ultimately generate a color red-green-blue ("RGB") image that is displayed to the surgeon and recorded as a video frame, if the surgical video is recorded. The image and signal processing steps may be referred to as the ISP pipeline and include a wide variety of processing stages to both correct for defects in the image sensor (e.g., bad pixels), to normalize the sensor output, to adjust pixel values, to remove noise, as well as ultimately convert from grayscale to RGB. An example of such an ISP pipeline is illustrated in FIG. 2. The example ISP pipeline 300 in FIG. 2 illustrates a typical ISP pipeline for a camera. The various blocks represent specific image or signal processing steps that are performed in sequence from the initial RAW sensor data output. Some or all of these blocks may employ ISP parameters that may be modified over time based on the output of the ML model(s), as discussed above with respect to FIG. 1. Thus, as the ML model(s) analyze video output by the endoscope and recognize scene types or scene features, the controller 120 may determine new ISP parameters based on the recognized scene types or scene features and provide the new ISP parameters to the endoscope, which updates its ISP pipeline to employ the new ISP parameters. Subsequent video frames will then be processed through the ISP pipeline using the updated ISP parameters, changing the appearance of the captured video frames and providing higher quality video to the surgeon at the user station 130.

Figure 3B:
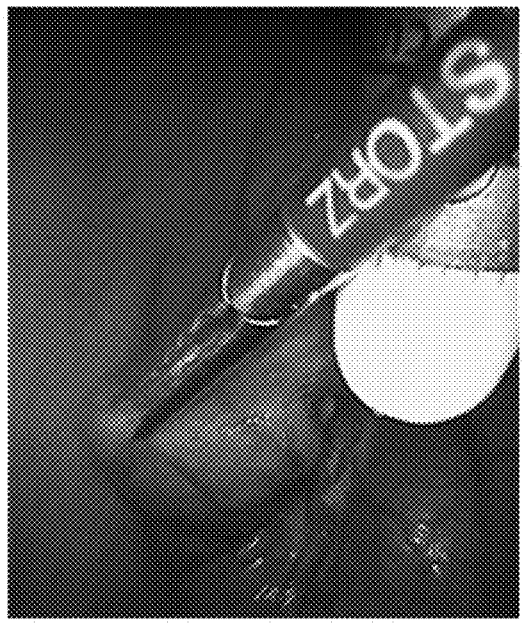
FIGS. 3A-3D show example images from surgical procedures illustrating different image quality issues.
Figure 3D:
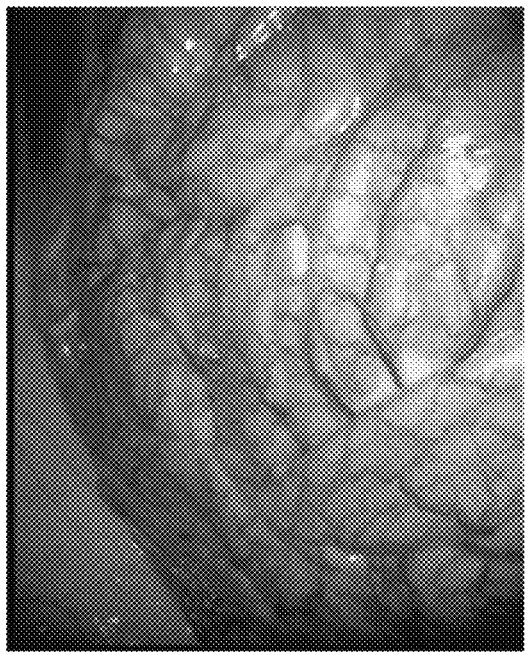
Figure 3A:
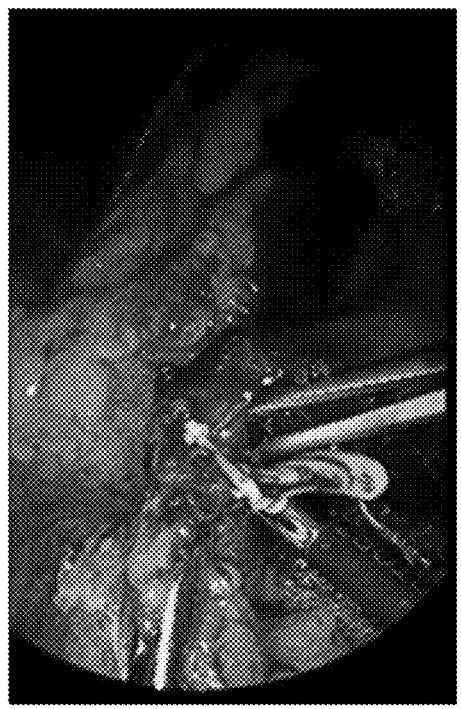
Figure 3C:
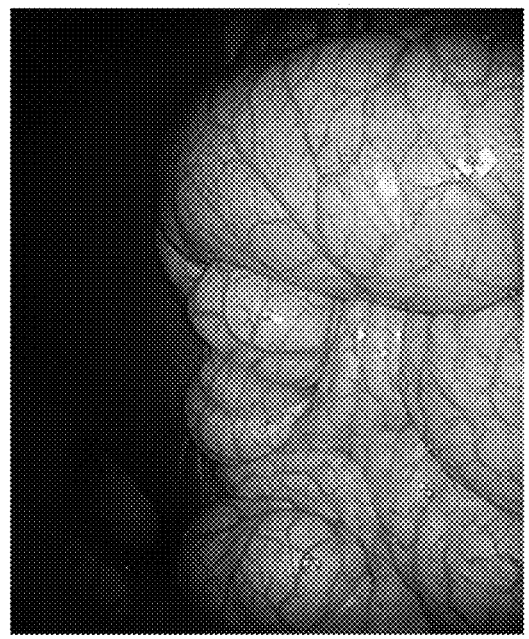

Using a static ISP pipeline, video captured during a surgery may have any number of image quality issues. FIGS. 3A-3D illustrate some of the issues with image quality that can arise. For example, FIG. 3A illustrates an illuminated scene that is overly dark due to a particular scene feature being present, i.e., blood in the scene, in this example. In contrast, FIG. 3B illustrates a scene in which the patient's tissue is underexposed due to the presence of a different scene feature, i.e., a highly reflective surgical tool in the scene. FIG. 3C illustrates an example where anatomical features in the scene near to the camera are well illuminated, but anatomy distant from the camera is overly dark due to the near field illumination affecting the ISP pipeline processing. Finally, FIG. 3D illustrates an image in which the scene provides excellent contrast; however, important anatomical features, i.e., blood vessels in this example, have poor quality contrast, resulting from the contrast settings for the remainder of the image. Thus, each of these figures illustrates scenarios in which changing ISP parameters for a camera to adjust to the scene could significantly improve image quality.

Figure 4:
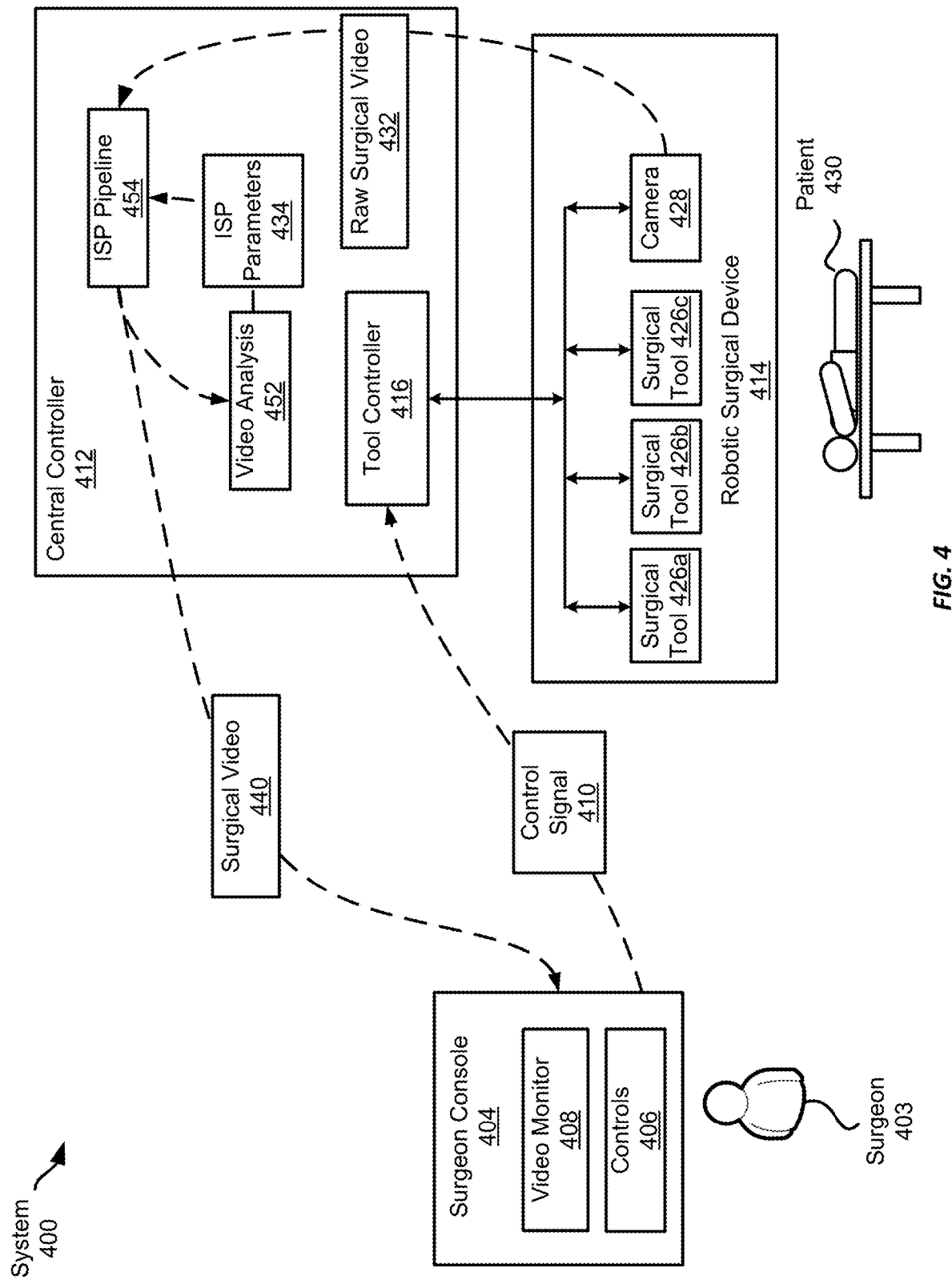
FIGS. 4-6 shows an example system for scene-adaptive image quality in surgical video.

Referring now to FIG. 4, FIG. 4 shows a more detailed view of an example system 400 for scene-adaptive image quality in surgical video. This example system 400 includes a robotic surgical device 414 configured to operate on a patient 430, and a central controller 412 to control the robotic surgical device 414. The system 400 also includes a surgeon console 404 connected to the central controller 412 and the robotic surgical device 414. The surgeon console 404 is operated by a surgeon 403 to control and monitor the surgeries performed using the robotic surgical device 414. In addition to these components, the system 400 might include additional stations (not shown in FIG. 4) that can be used by other personnel in the operating room, for example, to view surgery information, video, etc., sent from the robotic surgical device 414. In this example, the robotic surgical device 414, the central controller 412, the surgeon console 404 and other stations are connected directly to each other, though in some examples they may be connected using a network, such as a local-area network ("LAN"), a wide-area network ("WAN"), or any other networking topology known in the art that connects the various stations in the system 400.

The robotic surgical device 414 can be any suitable robotic system utilized to perform surgical procedures on a patient. For example, the robotic surgical device 414 may have one or more robotic arms connected to a base. The robotic arms may be manipulated by a tool controller 416, which may include one or more user interface devices, such as joysticks, knobs, handles, or other rotatable or translatable devices to effect movement of one or more of the robotic arms. The robotic arms may be equipped with one or more surgical tools to perform aspects of a surgical procedure, and different surgical tools may be exchanged during the course of the surgical procedure. For example, the robotic arms may be equipped with surgical tools 426a-426c. Each of the surgical tools can be controlled by the surgeon 403 through the surgeon console 404 and the tool controller 416.

In addition, the robotic surgical device 414 is equipped with one or more cameras 428, such as an endoscope camera, configured to provide a view of the operating site to guide the surgeon 403 during the surgery. In some examples, the camera 428 can be attached to one of the robotic arms of the robotic surgical device 414 controlled by the tool controller 416 as shown in FIG. 4. In other examples, the camera 428 can be attached to a mechanical structure of the robotic surgical device 414 that is separate from the robotic arms, such as a dedicated arm for carrying the camera 428.

Different robotic surgical devices 414 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one robotic surgical device 414 is depicted, any suitable number of robotic surgical devices may be employed within a system 400.

In some examples, robotic surgical devices (or a respective controller) may be configured to record data during a surgical procedure. For example, images and videos of the surgical procedures performed by the robotic surgical device 414 can also be recorded and stored for further use.

In the example shown in FIG. 4, surgical video 440 of a robotic surgical procedure captured by the camera 428 is also be transmitted to the surgeon console 404 and be displayed on a video monitor 408 in real time so that the surgeon 403 can view the procedure while the surgical tools 426 are being used to operate on the patient 430. In this example, the surgeon 403 uses the surgeon console 404 to control the surgical tools 426 and the camera 428, and uses controls 406 on the surgeon console 404 to maneuver the surgical tools 426 and camera 428 by sending corresponding control signals 410 to the tool controller 416.

As shown in FIG. 4, the controller 412 includes an ISP pipeline 454 and video analysis software 452 to process the raw surgical video 432 captured during the surgical procedure and to determine and provide new ISP parameters to be applied to the camera 428. As will be discussed in more detail below, the video analysis software 452 analyzes frames of the received video (e.g. surgical video 440) to recognize scene types or features captured in the video frames.

Raw surgical video 432 captured by the camera 428 is first processed by the ISP pipeline 454, which is implemented using a GPU in this example. The GPU applies the currently selected set of ISP parameters to the fully-configurable ISP pipeline and generates surgical video 440, which is then provided to the video analysis software 452 and to the surgeon console 404.

In this example, the video analysis software 452 employs one or more ML models that have been trained to recognize scene types or scene features, which may be anatomic (e.g., organs, adhesions, blood vessels, etc.), tools (e.g., scalpels, forceps, clamps, trocars, etc.), events (e.g., bleeding, smoking, etc.), or other features. Video frames are presented to the trained ML technique(s), which then recognize the scene types or features within the frames and output the identified scene types or features.

In some examples, an ML model may output probabilities related to recognized scene types or features. For example, an ML model may have been trained to recognize twenty different scene types. After being presented with a video frame as input, the ML model may output a group (or tuple) of twenty probability values, each of which corresponds to one of the trained scene types, with the cumulative total of all the outputted probabilities being 1 (or 100%). In an example using an ML model trained to recognized three scene types, a tuple output may resemble the following: (0.15, 0.67, 0.18), corresponding to scene types 1-3, respectively, and with probability values ranging from 0 to 1, representing probabilities from 0-100%. Similarly, a ML model trained to recognize different scene features may also output one or more probabilities associated with the trained scene features. Alternatively, the ML model(s) may output only probabilities associated with scene types or features above a predetermined threshold, or the top N probabilities (e.g., the top 3 probabilities). Further, in some examples, the ML model(s) may only output the most likely scene type or feature.

While this example employs one ML model to recognize scene types and one ML model to recognize scene features, it should be appreciated that multiple ML models may be used to recognize scene types or scene features. For example, one ML model may be trained on a particular class of scene types, while a different ML model may be trained on a different class of scene types. Similarly, one ML model may be trained on a particular class of scene features, while a different ML model may be trained on a different class of scene features. The central controller 412 may provide received video frames to each of the trained ML models to determine scene types or features.

During operation, the central controller 412 may receive video frames in real-time at a predetermined frame rate from the camera, e.g., 30 or 60 frames per second. Depending on the frame rate or the configuration of the central controller 412, it may process all received frames or only a subset of them. For example, the central controller 412 may provide 1 frame per second to the video analysis software 452 to determine scene types or features. Such a configuration may enable reasonable response time without requiring substantial processing resources. Some examples may employ different strategies to process video frames, such as processing as many frames as possible, e.g., by processing a one frame and, when processing on the frame is completed, processing the next available frame, irrespective of how many intervening frames have been captured.

After the video analysis software 452 has determined a scene type or a scene feature corresponding to a video frame, it determines one or more ISP parameters corresponding to the scene type or scene feature. In this example, the video analysis software 452 has access to a data store that stores sets of ISP parameters for each scene type the ML model is trained to recognize, as well as sets of ISP parameters for each scene feature the ML model is trained to recognize.

For example, if the ML model recognizes a bleeding event (a type of scene feature) at a particular location in a frame (e.g., as shown in FIG. 3A), it may obtain a set of ISP parameters with a modified auto-exposure setting to increase luminance in the auto-exposure ("AE") portion of the ISP pipeline. And while this may over-expose the other portions of the scene, the set of ISP parameters also include ISP parameters to modify the local tone mapping module to non-linearly map the intensities of anatomy at locations other than where the bleeding is identified to prevent overexposure. In a typical ISP pipeline, a bleeding event that only darkens a portion of the image may not be fully compensated by AE since auto-exposure operates on image-level statistics, rather than portions of the image. Thus, the system 400 is able to compensate for darkened portions of the scene without over-saturating the entire scene.

Alternatively, if the ML model recognizes a reflective instrument (another type of scene feature), or multiple reflective instruments, at a particular location in a frame e.g., as shown in FIG. 3B), it may obtain a set of ISP parameters with a modified auto-exposure setting to key only on the anatomy in the scene instead of the reflective instrument(s). At the same time, local tone mapping is adjusted to drastically dampen the strong reflections on the instruments to prevent eye fatigue and distractions. By modifying the parameters for these portions of the ISP pipeline, the system ensures that the anatomy of interest is well-illuminated and more accurately color represented, while simultaneously dampening the reflections from the instruments, which may be distracting or contribute to eye fatigue.

More generally, scenes may include features with widely varying dynamic ranges, or with very little variation in dynamic ranges. For example, if both a reflective tool and a bleeding event occur in the same frame, it can present dramatically different brightness levels in different parts of the same frame. Conversely, some scenes may have much lower dynamic ranges (e.g., the bowels shown in FIG. 3D). In some examples, the ML model may determine scene types based on detected dynamic ranges, e.g., having a high dynamic range (above a first threshold) or a low dynamic range (below a second threshold). Thus, the video analysis software 452 is able to adjust the ISP pipeline to improve contrast in a low dynamic range scene, while preventing over-darkening in high dynamic range scenes, such as discussed above with respect to reflective tools.

Thus, after determining a scene type or scene feature, the video analysis software 452 accesses the corresponding set of ISP parameters, and if only one scene type or feature is identified, uses the accessed set of ISP parameters without modification.

In some examples, however, the video analysis software 452 may determine multiple different scene types or features. As discussed above, in some examples, a tuple of probabilities may be received for a video frame. The video analysis software 452 may then select some or all of the corresponding scene types based on their respective probabilities, e.g., the probability satisfies a predetermined threshold. To determine a set of ISP parameters, the video analysis software 452 may access the sets of ISP parameters corresponding to each scene or feature. In some examples, it may only access the sets of ISP parameters corresponding to scenes or features with a sufficiently high probability.

After accessing the sets of ISP parameters, the video analysis software 452 combines them to generate a single set of ISP parameters. In this example, the video analysis software employs interpolation between ISP parameters in each of the accessed sets. For example, for ISP parameter 1, the values for that parameter from each accessed set of ISP parameters are weighted according to the corresponding probability of the scene type or feature. Each weighted parameter contributes to a parameter value according to its respective weight. In some examples, parameter values may not be interpreted linearly. For example some parameter values may affect image quality in a way that does not change linearly to human vision. The non-linearity may be characterized, e.g., as a curve, and used as the basis for interpolating ISP parameter values according to the non-linearity, e.g., along the curve.

After combining the sets of ISP parameters to generate one set of ISP parameters, the video analysis software 452 applies the ISP parameters to the ISP pipeline 454, which replaces the then-current ISP parameters employed by its ISP pipeline. Subsequently, video frames captured by the camera 428 are processed using the new ISP parameters and provided to the video analysis software 452 for analysis. By updating the ISP parameters based on the recognized scene types or parameters, video quality at the surgeon console 404 may be improved. Further, because the video analysis is performed repeatedly, the ISP parameters may be updated throughout the course of a surgical procedure in real-time (e.g., within a frame or a few frames of a scene type or feature change) or near-real-time (e.g., within a second or two of a scene type or feature change, enabling the system 400 to provide high quality video the surgeon 403.

While in this example, the ISP pipeline 454 is implemented in software at the central controller 412 and executed by a GPU, in other examples, the ISP pipeline may be implemented in hardware, e.g., in a system-on-a-chip ("SOC"), or as a combination of hardware and software. Further in some examples the ISP pipeline 454 may be implemented in the camera 428 itself. In some such examples, the ISP parameters 434 may be communicated to the camera 428 to update its ISP pipeline. Further, some examples may divide the ISP pipeline between the camera 428 and the central control 412, which may result in some ISP parameters being sent to the camera 428, while others are sent to the portion ISP pipeline 454 at the central controller.

It should be appreciated that although FIG. 4 illustrates the presented technique of scene-adaptive image quality in surgical video in the context of a system 400, it can be implemented in other types of systems and settings. For example, this technique can be implemented in a computing device separate from a system 400, such as by receiving a video feed from the endoscope via a networked connection.

Figure 5:
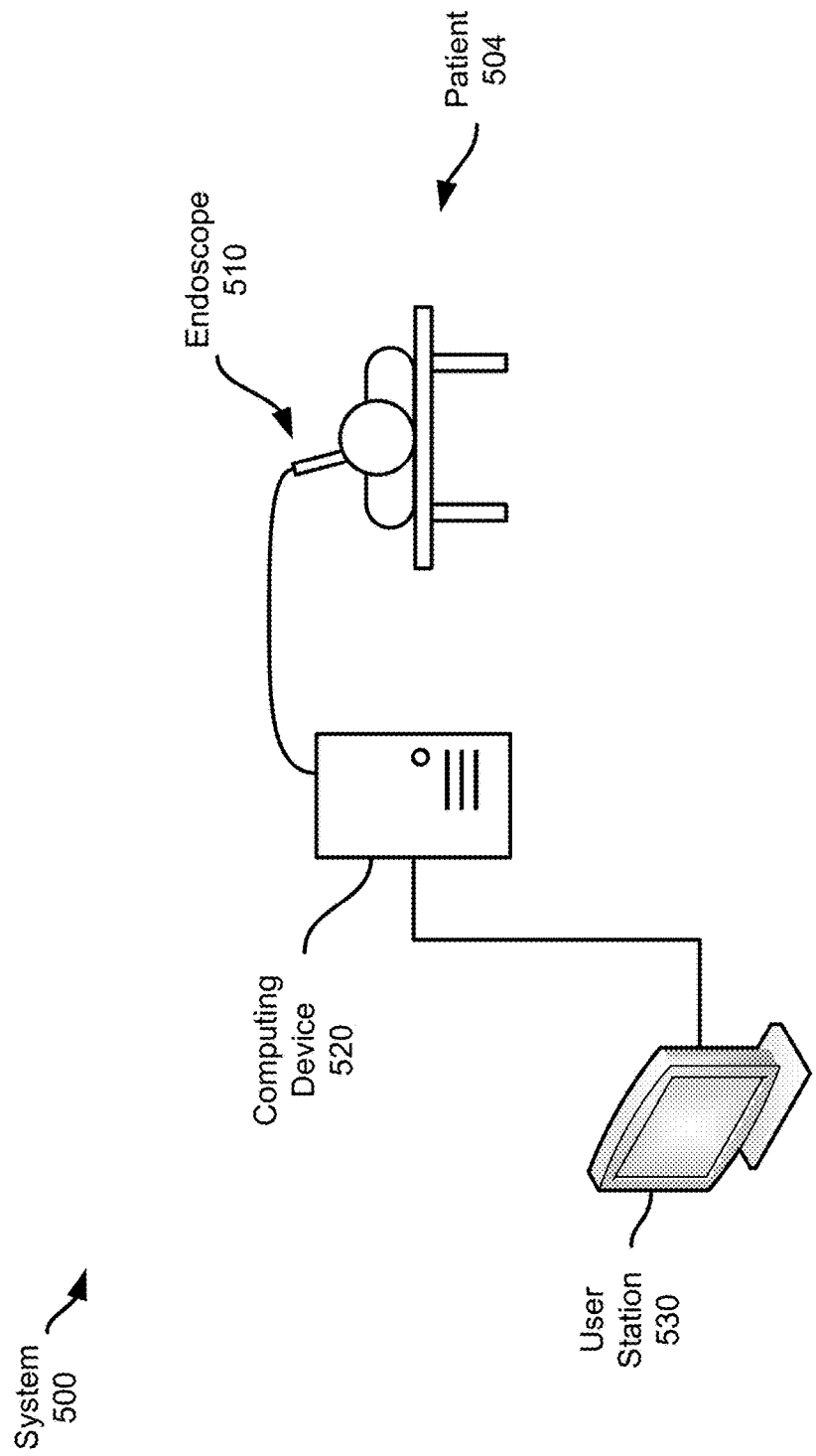

Referring now to FIG. 5, FIG. 5 shows an example system 500 for scene-adaptive image quality in surgical video. In this example, the system 500 includes a computing device 520 that is communicatively coupled to an endoscope 510, patient 504 and a user station 530. In this example, the system 500 is employed in a manual surgical procedure, without the use of a surgical robotic system, such as the example discussed above with respect to FIG. 4. Thus, during the surgery, the surgeon may manipulate the endoscope during the surgery to provide a suitable view for a particular task. Video frames captured by the endoscope 510 are communicated to the computing device 520, which executes an ISP pipeline, e.g., ISP pipeline 454, and video analysis software, e.g., video analysis software 452. In addition, video frames are communicated to the user station 530, which may be a separate computing device or may be a display device in some examples. The computing device 520 can update the ISP parameters in the ISP pipeline 454 based on analysis performed by the video analysis software to adjust the ISP pipeline.

Figure 6:
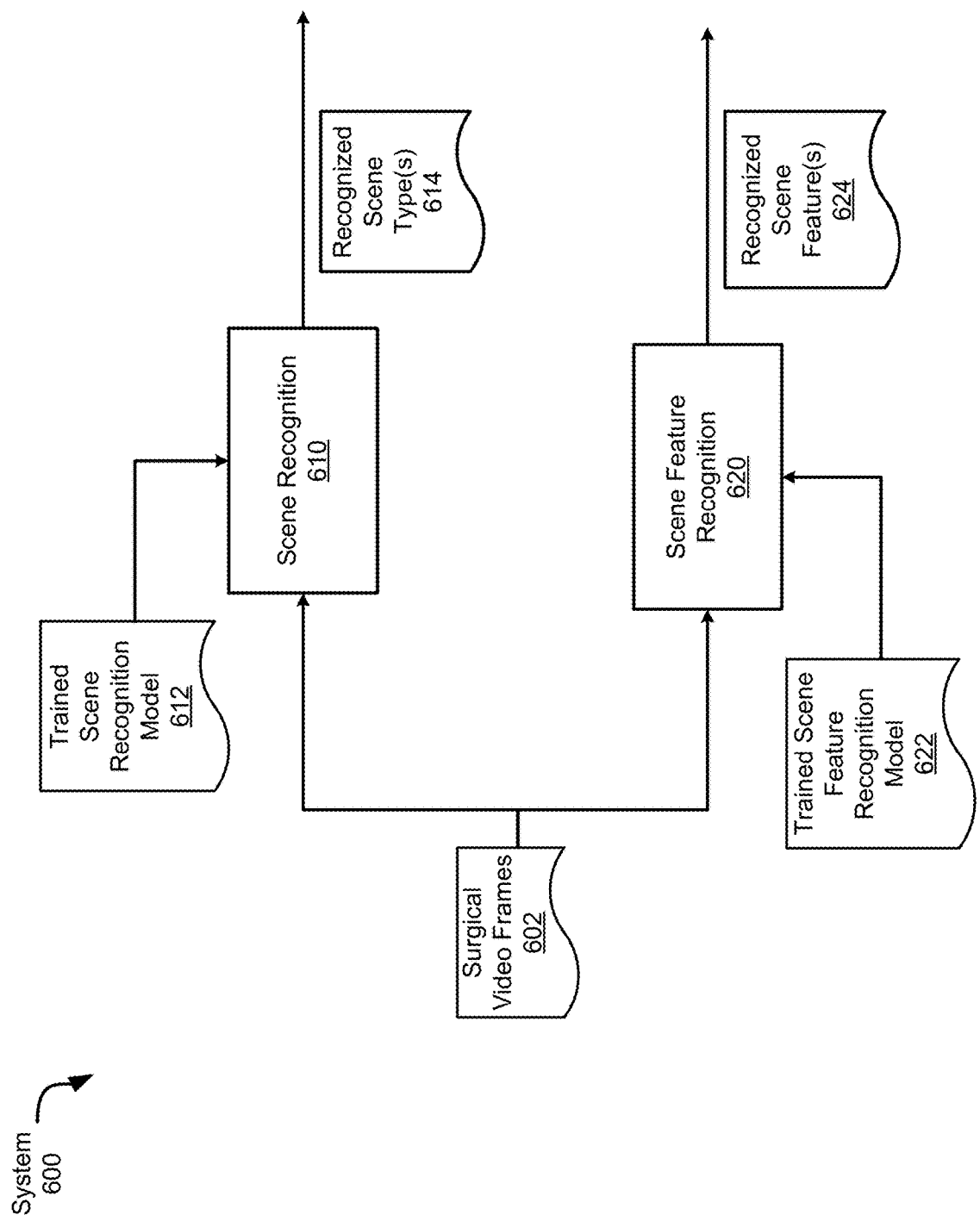

Referring now to FIG. 6, FIG. 6 shows an example system 600 for scene-adaptive image quality in a surgical video. The example system 600 includes both scene recognition software 610 and scene feature recognition software 620. The scene recognition software 610 in this example includes a trained scene recognition ML model 612, though in some examples, the scene recognition software 610 may include multiple trained scene recognition models. Similarly, the scene feature recognition software 620 includes a trained scene feature recognition ML model 622, though in some examples, the scene feature recognition software 620 may include multiple trained scene recognition models.

The example system 600 shown in FIG. 6 is embedded within video analysis software, such as video analysis software 452; however, in some examples, the system 600 may be a discrete software module that provides its output to video analysis software. In one such example the video analysis software may receive the output and determine a set of ISP parameters based on the received scene type(s) or scene feature(s) output by the system 600.

During operation, the scene recognition software 610 receives surgical video frames 602 and provides them to the trained scene recognition model 612, which processes the video frame 602 to generate one or more recognized scene types 614. Similarly, the scene feature recognition software 620 receives surgical video frames 602 and provides them to the trained scene feature recognition model 622, which processes the video frame 602 to generate one or more recognized scene feature types 624. In this example, the models 612, 622 each output a tuple having probabilities corresponding to each scene type or scene feature type the respective model 612, 622 is trained to recognize. The scene recognition software 610 obtains the tuples and outputs them for use by video analysis software, e.g., video analysis software 452, to determine a set of ISP parameters, such as discussed above with respect to FIG. 4. And while the ML models 612, 622 in this example output tuples, in some examples, ML models may only output the most likely recognized scene or scene feature type, e.g., the scene type or scene feature type with the highest probability. Still other variations are contemplated by this disclosure.

While the example system 600 shown in FIG. 6 includes two models, one each for scene recognition and scene feature recognition, in some examples, multiple models of either kind may be used. Further, in some examples, one ML model may be trained to recognized both scene types and scene feature types. In one such examples, scene recognition software 610 and scene feature recognition software 620 may be a single software module accessing a single trained ML model to obtain tuples representing probabilities of scene types or scene feature types.

Figure 7:
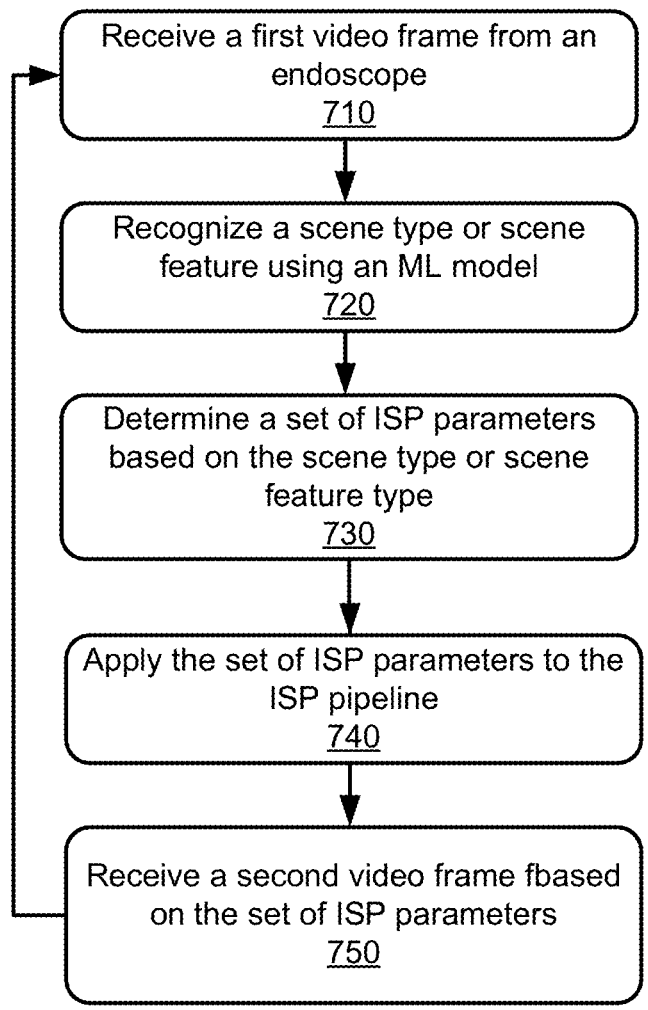
FIG. 7 shows an example method for scene-adaptive image quality in surgical video.

Referring now to FIG. 7, FIG. 7 shows an example method 700 for scene-adaptive image quality in surgical video. This example method 700 will be described with respect to the systems shown in FIGS. 4 and 6; however, any suitable system according to this disclosure may be employed.

At block 710, the video analysis software 452, executed by the controller 412, receives a first video frame from an endoscope, the first video frame generated from a first raw image captured by an image sensor of the endoscope and processed by an image signal processing ("ISP") pipeline, e.g., ISP pipeline 454, having a plurality of ISP parameters. As discussed above, an endoscope may employ an image sensor that outputs raw pixel data that is processed by an ISP pipeline to generate an RGB image that is transmitted as a frame of video. Further, as discussed above, the ISP pipeline may be executed at the controller, on the endoscope, divided between the two, or at any other suitable computing device. In this example, video frames are received both by the controller 412 and the surgeon console 404. In some examples, the video frames may be sent to any suitable computing device, whether as a part of a robotic surgery system or as a standalone computing device.

At block 720, the video analysis software 452 recognizes a first scene type or scene feature type using a trained ML model, e.g., one of trained ML models 612, 622. As discussed above with respect to FIG. 6, a video frame 602 from an endoscope may be provided to scene recognition software 610 or scene feature recognition software 620 to recognize a scene type or scene feature type. Further, as discussed above, the output of the ML model(s) may be a single identified scene type or scene feature type, or it may be a tuple representing probabilities that the video frame depicts a particular scene type or scene feature type. Thus, the video analysis software 452 may recognize the scene type or scene feature type by selecting a single scene type or scene feature type, by outputting probabilities that the video frame depicts different scene types or scene feature types, or any other suitable format.

In some examples, the video analysis software 452 may recognize both a scene type and a scene feature type. For example, while some example systems may only include trained ML models to recognize scene types or scene feature types, without an ML model capable of recognizing the other, some examples may include one or more models to recognize scene types and scene feature types, e.g., as depicted in FIG. 6 or as described above.

At block 730, the video analysis software 452 determines a set of ISP parameters based on the scene type or the scene feature type. In some examples, the video analysis software 452 may only determine a scene type or a scene feature type, and further the ML model may only identify a single scene type or scene feature type. In one such example, the video analysis software 452 accesses a data store and identifies and retrieves a set of ISP parameters corresponding to the identified scene type or scene feature type.

However, in some examples, the video analysis software 452 may identify a scene type or scene feature type, but may obtain probabilities associated with multiple different scene or feature types, such as in examples where the ML model(s) output tuples of probabilities corresponding to scene types or features. After obtaining the multiple probabilities, the video analysis software 452 may discard scene types or scene feature types with associated probabilities that do not satisfy a pre-determined threshold (e.g., 25%). Alternatively, the video analysis software 452 may determine a set of ISP parameters based on all probabilities output by the ML model 612, 622.

If probabilities for multiple scene types or scene feature types are used, the video analysis software 452 may obtain sets of ISP parameters corresponding to the scene types that were not discarded based on probabilities. The video analysis software 452 may then combine corresponding parameter values from the various sets of ISP parameters to determine a single set of ISP parameters. In this example, the video analysis software 452 weights each parameter value in each set of ISP parameters based on the probability for the corresponding scene type or scene feature type. Corresponding weighted values for each ISP parameter in the sets of ISP parameters may then be summed and divided by the sum of the weights of the ISP parameter sets to obtain an interpolated parameter value for each ISP parameter. Alternatively, rather than employing a weighted interpolated value, the video analysis software 452 may access curves or other non-linear characterizations associated with one or more ISP parameters and interpolate ISP parameter values from the different sets of ISP parameters along such curves or non-linear characterizations, based on the respective probabilities.

In some examples that recognize both scene type and scene feature types, the video analysis software 452 may determine a set of ISP parameters for the scene type and another set of ISP parameters for the scene feature type, as discussed above. These two sets of ISP parameters may then be combined, such as according to a predetermined ratio or by interpolating between the two sets as discussed above, e.g., by weighted interpolation, linearly or non-linearly. If multiple sets of ISP parameters for multiple scene types or scene features are determined, they also may be combined generally as discussed above. Thus, at block 730, the video analysis software 452 can combine ISP parameter sets in any suitable way to obtain a single set of ISP parameters.

At block 740, the video analysis software 452 applies the set of ISP parameters to the ISP pipeline. In this example, the controller 412 applies the set of ISP parameters to the ISP pipeline 454 executed at the central controller 412; however, in some examples, it may transmit the set of ISP parameters to the endoscope along with an indication to update the then-current ISP parameters used by the endoscope 428. Further, in examples with a distributed ISP pipeline, the set of ISP parameters may be sent to the respective portions of the ISP pipeline according to which parameters are applied at which portion.

At block 750, the controller 412 receives another video frame from the endoscope 428 and applies the new set of ISP parameters using the ISP pipeline. The controller 412 provides the new video frame to the video analysis software 452 to restart the method 700 at block 710.

Examples according to this disclosure may repeatedly execute the functionality in blocks 710-750 to update ISP parameters over time during a surgical procedure. The rate at which example methods may be repeated may vary from every video frame to only a sampled set of video frames.

While the example discussed above was within the context of a robotic surgical system 400, it should be appreciated that use of such a robotic surgical system is not required. Instead, a traditional minimally-invasive surgery may be performed manually and employ an endoscope, such as by using the example system 500 shown in FIG. 5.

Figure 8:
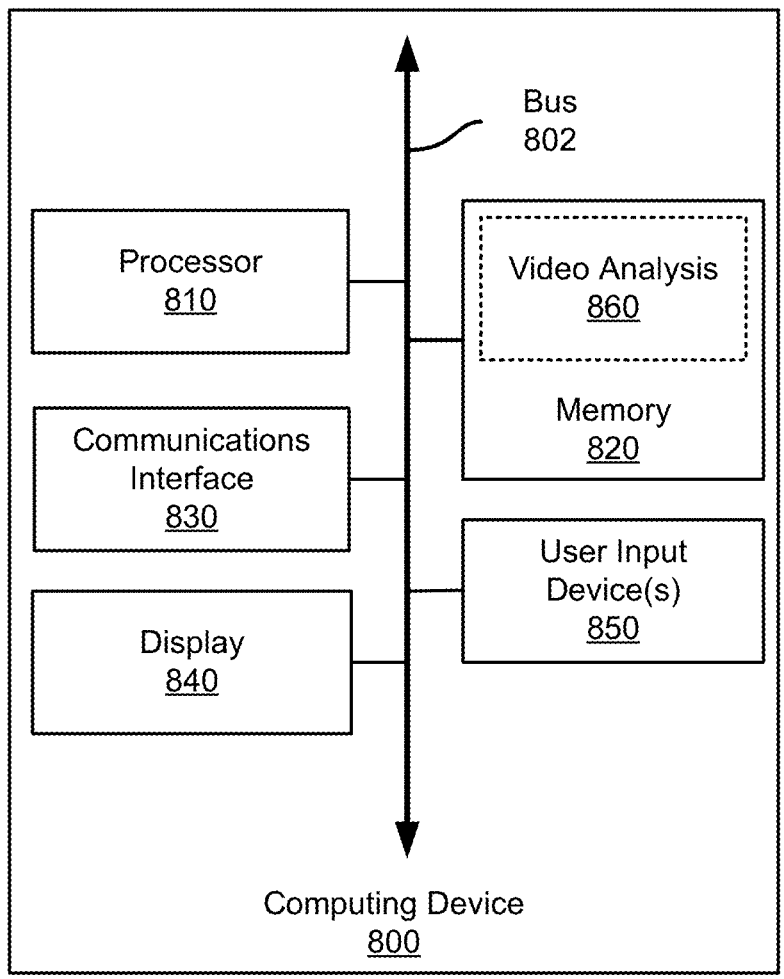
FIG. 8 shows an example computing device suitable for use with systems and methods for scene-adaptive image quality in surgical video according to this disclosure.

Referring now to FIG. 8, FIG. 8 shows an example computing device 800 suitable for use in example systems or methods for scene-adaptive image quality in surgical video according to this disclosure. The example computing device 800 includes a processor 810 which is in communication with the memory 820 and other components of the computing device 800 using one or more communications buses 802. The processor 810 is configured to execute processor-executable instructions stored in the memory 820 to perform one or more methods for scene-adaptive image quality in surgical video according to different examples, such as part or all of the example method 700 described above with respect to FIG. 7. In this example, the memory 820 includes a video analysis system 860, such as the example video analysis software 452 or system 500 shown in FIGS. 4 or FIG. 5. In addition, the computing device 800 also includes one or more user input devices 850, such as a keyboard, mouse, touchscreen, microphone, etc., to accept user input; however, in some examples, the computing device 800 may lack such user input devices, such as remote servers or cloud servers. The computing device 800 also includes a display 840 to provide visual output to a user. However, it should be appreciated that user input devices or displays may be optional in some examples.

The computing device 800 also includes a communications interface 840. In some examples, the communications interface 830 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) of graphics processing unit (GPU) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
    receiving a first video frame from an endoscope, the first video frame generated from a first raw image captured by an image sensor of the endoscope and processed by an image signal processing ("ISP") pipeline having a plurality of ISP parameters;
    recognizing, using a trained machine learning ("ML") model, a first scene type or a first scene feature type based on the first video frame;
    determining a first set of ISP parameters based on the first scene type or the first scene feature type;
    applying the first set of ISP parameters to the ISP pipeline; and
    receiving a second video frame from the endoscope, the second video frame generated from a second raw image captured by the image sensor and processed by the ISP pipeline using the first set of ISP parameters.

2. The method of claim 1, wherein recognizing the first scene type or the first scene feature type comprises obtaining, using the trained ML model, a plurality of probabilities, each probability corresponding to a different scene type of a plurality of scene types or a different scene feature type of a plurality of scene feature types, each probability indicating a likelihood that the first video frame is of the corresponding scene type or scene feature type.

3. The method of claim 2, further comprising determining a subset of the plurality of scene types or a subset of the plurality of scene feature types based on respective probabilities satisfying a threshold.

4. The method of claim 2, wherein determining a first set of ISP parameters comprises:
obtaining a plurality of sets of ISP parameters, each set of ISP parameters of the plurality of sets of ISP parameters corresponding to a scene type of the plurality of scene types or to a scene feature type of the plurality of scene feature types; and
generating the first set of ISP parameters based on interpolating between the plurality of sets of ISP parameters.

5. The method of claim 4, wherein the plurality of sets of ISP parameters comprises a second set of ISP parameters and a third set of ISP parameters, and wherein each of the second and third sets of ISP parameters comprises values for a first ISP parameter and a second ISP parameter, wherein:
the value for the first ISP parameter of the second set of ISP parameters is different than the value for the first ISP parameter of the third set of ISP parameters; and
the value for the second ISP parameter of the second set of ISP parameters is different than the value for the second ISP parameter of the third set of ISP parameters; and
wherein generating the first set of ISP parameters comprises:
interpolating a first interpolated parameter value based on the value for the first ISP parameter of the second set of ISP parameters and the value for the first ISP parameter of the third set of ISP parameters according to a first interpolation technique; and
interpolating a second interpolated parameter value based on the value for the second ISP parameter of the second set of ISP parameters and the value for the second ISP parameter of the third set of ISP parameters according to a second interpolation technique.

6. The method of claim 5, wherein the first interpolation technique is different from the second interpolation technique.

7. The method of claim 1, further comprising:
identifying, using a second trained ML model, a scene feature type based on the first video frame;
determining a scene feature set of ISP parameters based on the first scene feature;
combining the scene feature set of ISP parameters with the first set of ISP parameters; and
wherein applying the first set of ISP parameters to the ISP pipeline comprises applying the combination of the scene feature set of ISP parameters with the first set of ISP parameters to the ISP pipeline.

8. The method of claim 7, wherein the first scene feature comprises a tool or an anatomical feature.

9. A system comprising:
a non-transitory computer-readable medium; and
one or more processors communicatively coupled to the non-transitory computer-readable medium and configured to execute processor-executable instructions stored in the non-transitory computer-readable medium to:
receive a first video frame from an endoscope, the first video frame generated from a first raw image captured by an image sensor of the endoscope and processed by an image signal processing ("ISP") pipeline having a plurality of ISP parameters;
recognize, using a trained machine learning ("ML") model, a first scene type or a first scene feature type based on the first video frame;
determine a first set of ISP parameters based on the first scene type or the first scene feature type;
apply the first set of ISP parameters to the ISP pipeline; and
receive a second video frame from the endoscope, the second video frame generated from a second raw image captured by the image sensor and processed by the ISP pipeline using the first set of ISP parameters.

10. The system of claim 9, wherein the one or more processors are configured to execute further processor-executable instructions stored in the non-transitory computer-readable medium to obtain, using the trained ML model, a plurality of probabilities, each probability corresponding to a different scene type of a plurality of scene types or a different scene feature type of a plurality of scene feature types, each probability indicating a likelihood that the first video frame is of the corresponding scene type or scene feature type.

11. The system of claim 10, wherein the one or more processors are configured to execute further processor-executable instructions stored in the non-transitory computer-readable medium to determine a subset of the plurality of scene types or a subset of the plurality of scene feature types based on respective probabilities satisfying a threshold.

12. The system of claim 10, wherein the one or more processors are configured to execute further processor-executable instructions stored in the non-transitory computer-readable medium to:
obtain a plurality of sets of ISP parameters, each set of ISP parameters of the plurality of sets of ISP parameters corresponding to a scene type of the plurality of scene types or to a scene feature type of the plurality of scene feature types; and
generate the first set of ISP parameters based on interpolating between the plurality of sets of ISP parameters.

13. The system of claim 12, wherein the plurality of sets of ISP parameters comprises a second set of ISP parameters and a third set of ISP parameters, and wherein each of the second and third sets of ISP parameters comprises values for a first ISP parameter and a second ISP parameter, wherein:
the value for the first ISP parameter of the second set of ISP parameters is different than the value for the first ISP parameter of the third set of ISP parameters; and
the value for the second ISP parameter of the second set of ISP parameters is different than the value for the second ISP parameter of the third set of ISP parameters; and
wherein the one or more processors are configured to execute further processor-executable instructions stored in the non-transitory computer-readable medium to:
interpolate a first interpolated parameter value based on the value for the first ISP parameter of the second set of ISP parameters and the value for the first ISP parameter of the third set of ISP parameters according to a first interpolation technique;
interpolate a first interpolated parameter value based on the value for the second ISP parameter of the second set of ISP parameters and the value for the second ISP parameter of the third set of ISP parameters according to a second interpolation technique; and generate the first set of ISP parameters based on the first and second interpolated parameter values.

14. The system of claim 13, wherein the first interpolation technique is different from the second interpolation technique.

15. The system of claim 9, wherein the one or more processors are configured to execute further processor-executable instructions stored in the non-transitory computer-readable medium to:
   identify, using a second trained ML model, a scene feature type based on the first video frame;
   determine a scene feature set of ISP parameters based on the first scene feature;
   combine the scene feature set of ISP parameters with the first set of ISP parameters; and
   apply the combination of the scene feature set of ISP parameters with the first set of ISP parameters to the ISP pipeline.

16. The system of claim 15, wherein the first scene feature comprises a tool or an anatomical feature.

17. A non-transitory computer-readable medium comprising processor-executable instructions configured to cause one or more processors to:
   receive a first video frame from an endoscope, the first video frame generated from a first raw image captured by an image sensor of the endoscope and processed by an image signal processing ("ISP") pipeline having a plurality of ISP parameters;
   recognize, using a trained machine learning ("ML") model, a first scene type or a first scene feature type based on the first video frame;
   determine a first set of ISP parameters based on the first scene type or the first scene feature type;
   apply the first set of ISP parameters to the ISP pipeline; and
   receive a second video frame from the endoscope, the second video frame generated from a second raw image captured by the image sensor and processed by the ISP pipeline using the first set of ISP parameters.

18. The non-transitory computer-readable medium of claim 17, wherein the one or more processors are configured to execute further processor-executable instructions stored in the non-transitory computer-readable medium to obtain, using the trained ML model, a plurality of probabilities, each probability corresponding to a different scene type of a plurality of scene types or a different scene feature type of a plurality of scene feature types, each probability indicating a likelihood that the first video frame is of the corresponding scene type or scene feature type.

19. The non-transitory computer-readable medium of claim 18, wherein the one or more processors are configured to execute further processor-executable instructions stored in the non-transitory computer-readable medium to determine a subset of the plurality of scene types or a subset of the plurality of scene feature types based on respective probabilities satisfying a threshold.

20. The non-transitory computer-readable medium of any of claim 18, wherein the one or more processors are configured to execute further processor-executable instructions stored in the non-transitory computer-readable medium to:
   obtain a plurality of sets of ISP parameters, each set of ISP parameters of the plurality of sets of ISP parameters corresponding to a scene type of the plurality of scene types or to a scene feature type of the plurality of scene feature types; and
   generate the first set of ISP parameters based on interpolating between the plurality of sets of ISP parameters.

21. The non-transitory computer-readable medium of claim 20, wherein the plurality of sets of ISP parameters comprises a second set of ISP parameters and a third set of ISP parameters, and wherein each of the second and third sets of ISP parameters comprises values for a first ISP parameter and a second ISP parameter, wherein:
   the value for the first ISP parameter of the second set of ISP parameters is different than the value for the first ISP parameter of the third set of ISP parameters; and
   the value for the second ISP parameter of the second set of ISP parameters is different than the value for the second ISP parameter of the third set of ISP parameters;
and
wherein the one or more processors are configured to execute further processor-executable instructions stored in the non-transitory computer-readable medium to:
   interpolate a first interpolated parameter value based on the value for the first ISP parameter of the second set of ISP parameters and the value for the first ISP parameter of the third set of ISP parameters according to a first interpolation technique;
   interpolate a first interpolated parameter value based on the value for the second ISP parameter of the second set of ISP parameters and the value for the second ISP parameter of the third set of ISP parameters according to a second interpolation technique; and
   generate the first set of ISP parameters based on the first and second interpolated parameter values.

22. The non-transitory computer-readable medium of claim 21, wherein the first interpolation technique is different from the second interpolation technique.

23. The non-transitory computer-readable medium of claim 17, wherein the one or more processors are configured to execute further processor-executable instructions stored in the non-transitory computer-readable medium to:
   identify, using a second trained ML model, a scene feature type based on the first video frame;
   determine a scene feature set of ISP parameters based on the first scene feature;
   combine the scene feature set of ISP parameters with the first set of ISP parameters; and
   apply the combination of the scene feature set of ISP parameters with the first set of ISP parameters to the ISP pipeline.

24. The non-transitory computer-readable medium of claim 23, wherein the first scene feature comprises a tool or an anatomical feature.

* * * * *